United States Patent [19]
Culbertson

[11] 3,963,703
[45] June 15, 1976

[54] TRIALKYLAMMONIUM -N-[β(1-AZIRIDINYL)] PROPIONOYLIMINES

[75] Inventor: Billy M. Culbertson, Worthington, Ohio

[73] Assignee: Ashland Oil, Inc., Ashland, Ky.

[22] Filed: Sept. 13, 1971

[21] Appl. No.: 180,098

[52] U.S. Cl. .............................. 260/239 E; 526/50; 526/263
[51] Int. Cl.² ............... C07D 203/12; C07D 295/14
[58] Field of Search ................... 260/239 E

[56] References Cited
UNITED STATES PATENTS

| | | | |
|---|---|---|---|
| 2,626,931 | 1/1953 | Bestian et al. | 260/239 E |
| 3,485,806 | 12/1969 | Bloomquist et al. | 260/80.3 N |

*Primary Examiner*—Alton D. Rollins

[57] ABSTRACT

A class of trialkylammonium -N-[β (1-aziridinyl)] propionoylimines and methods for preparing the same are described. These compounds find particular usefulness in the polymer art either as monomers, difunctional cross-linking agents or as modifiers for a variety of polymeric compositions containing active acid hydrogen atoms.

11 Claims, No Drawings

TRIALKYLAMMONIUM -N-[β(1-AZIRIDINYL)] PROPIONOYLIMINES

BACKGROUND OF THE INVENTION

1. Field of the Invention

This invention relates to a novel class of aziridinyl substituted aminimide compounds.

2. Description of the Prior Art

The ethylenimines or aziridines have been proposed by the prior art as useful compounds in the preparation of polymeric compositions. They can serve as monomers in the production of polymers and also can be used advantageously in chemically modifying thermoplastic polymers containing active acid hydrogen atoms by providing a pendant secondary amino group at such sites.

Compounds containing the aminimide structure

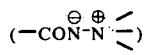

likewise have been proposed as useful intermediates in the formulation of polymeric compositions. The inclusion of the aminimide grouping into the structure of either the condensation or addition type polymers enhances the hydrophilic characteristics of the resultant polymer, which property is desirably sought in many utilitarian applications of such polymers. Also, by virtue of the ability of the aminimide grouping to thermolytically rearrange to the isocyanate structure, one can readily prepare polymeric type isocyanates which are advantageously adapted for providing thermoset resinous compositions.

SUMMARY OF THE INVENTION

In accordance with this invention, a class of difunctional compounds are provided for the first time wherein one of the functional groups is the aziridinyl radical and the other is the aminimide radical.

The compounds of the present invention are broadly represented by the following structural formula:

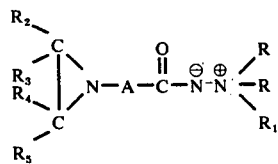

wherein A represents the ethylene or propylene radical; R is alkyl; $R_1$ is alkyl or hydroxyalkyl; and $R_2$, $R_3$, $R_4$ and $R_5$ each represents hydrogen, aryl or alkyl.

A noteworthy advantage residing in the practice of this invention is that such permits the realization of predominately polyethylenimine based polymer systems having a substantially higher molecular weight than that which can be attained solely through an aziridine ring opening polymerization mechanism.

Another advantage is that the use of an aziridinyl substituted aminimide to modify a thermoplastic polymer containing an acid hydrogen atom provides for a more versatile type of modification than that which can be achieved through the use of an ethylenimine wherein the N-substituent is an alkyl group.

Still another important advantage of the invention is that it affords a way of obtaining carbon-to-carbon addition polymers having pendant primary isocyanate groups from whence thermoset cross-links can be readily prepared.

DESCRIPTION OF THE PREFERRED EMBODIMENTS

The initial step of a process applicable for preparing the novel aziridinyl aminimides of this invention consists of effecting the Michael addition of an acrylate, methacrylate or crotonate with an aziridine. In accordance with the aforesaid process the lower alkyl esters of the contemplated acids are preferred with the methyl ester of the selected vinyl acid being particularly preferred.

As indicated, a variety of aziridines can be used in deriving the Michael adduct. These aziridines are represented by the following structural formula:

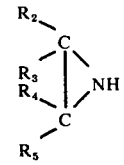

wherein $R_2$, $R_3$, $R_4$ and $R_5$ are either hydrogen, aryl or alkyl. The term "aryl" as employed herein is meant to define an organic radical in which the unsatisfied valence is at a carbon atom of the aromatic nucleus. Likewise, the term is embracive of those compounds wherein the aromatic nucleus contains other substituents besides hydrogen, such as a halo substituent, alkyl group and the like. An enumeration of representative aziridines for deriving the Michael addition product is as follows: ethylenimine, 2-methyl-ethylenimine, 2-ethyl-ethylenimine, 2,2-dimethyl-ethylenimine, 2,3-dimethyl-ethylenimine, 2,2,3-trimethyl-ethylenimine, 2,2-dimethyl-3-propyl-ethylenimine, 2-butyl-ethylenimine, 2,3-dipropyl-ethylenimine, 2-phenyl-ethylenimine, 2,3-diphenyl-ethylenimine, 2-ethyl-2-phenyl-ethylenimine, 2-ethyl-2-phenyl-3-methyl-ethylenimine, 2-propyl-2-phenyl-ethylenimine, 2-tolyl-ethylenimine, 2-xylyl-ethylenimine, etc. The preferred aziridines are ethylenimine and 2-methyl-ethylenimine.

The Michael addition reaction of the aziridine with the contemplated vinyl esters can be conveniently conducted in an alcoholic solvent medium. The lower alkanols are preferred for this purpose. The Michael addition yields are excellent since the aziridines are strong enough bases so that this reactant serves to auto-catalyze the reaction. Preferably in carrying out the addition reaction, a stoichiometric proportion of the aziridine to the vinyl ester is observed.

Two alternate ways have been developed recently for converting a carboxylic acid ester to the corresponding tertiary amine mono-imide or mono-aminimide. These methods find applicability in deriving the aziridinyl aminimides of this invention as the contemplated Michael addition products bear a carboxylate grouping. One of these methods consists of reacting the Michael addition product with a trialkyl hydrazinium halide, preferably the chloride salt, in the presence of a strong base to yield the desired derivative. Since the reaction of an ester with a hydrazinium salt is a nucleophilic displacement type reaction, it is preferable to carry out the reaction in a hydroxylic solvent. The preferred hydroxylic solvents are the lower alkanols, especially isopropanol. Further details relative to this method for deriving an aminimide can be found in U.S. Ser. No. 14,668, filed Feb. 26, 1970, now U.S. Pat. No. 3,706,800.

The other method referred to for deriving the aziridinyl aminimides of this invention consists of reacting a carboxylic acid ester, in the present context the Michael addition product, with an unsymmetrical disubstitued hydrazine, preferably a dialkyl hydrazine and a mono-epoxide. Further details concerning this method and the applicable substituted hydrazine and epoxide reactants can be found in U.S. Pat. No. 3,485,806. Additionally, the working examples provided herein are exemplary of the manner for obtaining the contemplated aziridinyl aminimides.

In order to illustrate to those skilled in the art the best mode contemplated for carrying out the present invention, the following working examples are set forth. As indicated, these examples are presented primarily by way of illustration and accordingly any enumeration of details contained therein should not be construed as a limitation on the invention except to the extent expressed in the appended claims. All parts and percentages given are on a weight basis unless otherwise indicated.

EXAMPLE I

This example illustrates the preparation of 1, 1-dimethyl-1-(2-hydroxypropyl) ammonium -N-[β(1-aziridinyl)] propionoylimine.

Methyl acrylate was treated with ethylenimine in accordance with the procedure outlined in H. Bestian, Ann. 566, 210 (1950) to prepare methyl β(1-aziridinyl) propionate in excellent yield.

A pressure vessel was charged with 38.7 parts of methyl β-(1-aziridinyl) propionate and 60 parts anhydrous alcohol. Distilled 1, 1-dimethyl hydrazine in the amount of 21 parts and 20.3 parts of cold propylene oxide were added and the vessel sealed. The contents of the reaction vessel were stirred at room temperature for 3 days. Evaporation of solvent and other volatiles at 0.1 mm, Hg, afforded 70 parts (theory, 75 parts) of a very viscous, light yellow oil whose infrared spectrum exhibited the expected strong aminimide absorption band at 1575cm$^{-1}$ and other absorption bands attributable to the aziridinyl structure. Elementary analysis confirmed the following assigned structure:

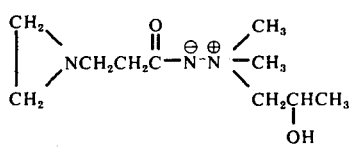

EXAMPLE II

Methyl β[1-(2-methylarziridinyl)] propionate was prepared from methylacrylate and 2-methyl-ethylenimine (propylenimine) following the procedure used in Example I. Likewise, the resultant Michael addition product was reacted with 1, 1-dimethyl hydrazine and propylene oxide in anhydrous isopropyl alcohol according to the procedure outlined in Example I, again employing substantially stoichiometric proportions of the reactants. The resultant reaction mixture upon evaporation of the solvent afforded a very viscous, faintly yellow liquid in 83% yield which was identified as 1, 1-dimethyl-1(2-hydroxypropyl) ammonium -N-β[1-(2-methylarziridinyl)] propionoylimine.

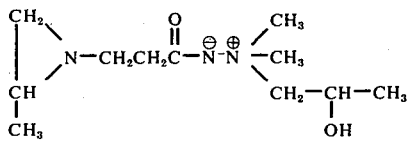

EXAMPLE III

The methyl β(1-aziridinyl) propionate of Example I was reacted with 1, 1-dimethyl hydrazine and 2-3-epoxypropylalcohol in accordance with the procedure used in the previous examples to obtain 1, 1-dimethyl-(2, 3-dihydroxypropyl ammonium -N-[β(1-aziridinyl)] propionoylimine corresponding to the following structural formula:

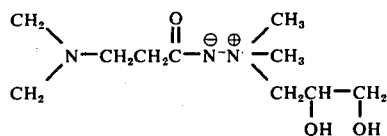

EXAMPLE IV

Using the procedure of the previous examples, the Michael addition product of Example II was treated with 1, 1-dimethyl hydrazine and 2, 3-epoxypropylalcohol to provide 1, 1-dimethyl-2, 3-dihydroxypropyl) ammonium -N- β[1-(2-methylaziridinyl) ] propionoylimine. Analysis data obtained for the resultant product confirmed the following structure:

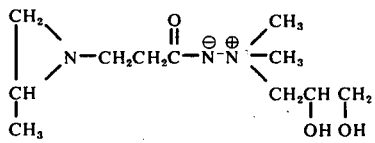

EXAMPLE V

This example is illustrative of a manner in which the aziridinyl aminimides of this invention can be utilized to modify polymers containing pendant carboxylic acid groups.

A terpolymer of styrene, butyl acrylate and acrylic acid was prepared by the conventional copolymerization of a 50:40:10 molar mixture of the respective monomers in xylene using azobisisobutyronitrile initiator. Titration of the polymer with base indicated the polymer had an equivalent weight of 2830 (theory, 2780).

To the terpolymer solution (283 grams, 0.1 e.q.) was added a xylene solution of the aziridinyl aminimide of Example I in the amount of 21.5 g. (0.1 eq.). The mixture was stirred at room temperature for two days. Infrared spectra studies indicated that the carboxylic acid groups of the terpolymer reacted with the aziridinyl residue of the aminimide, i.e., absorption bands indicative of free carboxylic groups and the aziridinyl ring structure vanished from the final infrared spectrum of the reaction product. The infrared spectrum of the product exhibited the expected strong aminimide absorption band at 1575cm$^{-1}$. Further % nitrogen (Found: N, 1.99%) for the isolated and purified polymer supported addition of the aziridinyl compound at the carboxylic acid groups along the polymer backbone (theory: N, 1.8%).

The treated polymer provided excellent hard, clear films when cast on aluminum and glass panels and air dried. When thermolyzed at 160°C. for 30 minutes, the cast air dried films became insoluble and the infrared spectrum of the cross-linked polymer indicated the absence of the aminimide absorption band at 1575cm$^{-1}$ and the presence of a new band attributable to urethane or urea residues.

What is claimed is:

1. A compound of the formula

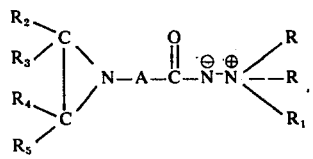

wherein A represents the ethylene or propylene radical; R is alkyl; $R_1$ is alkyl or hydroxyalkyl; and $R_2$, $R_3$, $R_4$ and $R_5$ each represents hydrogen, aryl or alkyl.

2. A compound in accordance with claim 1 wherein A represents the ethylene radical.

3. A compound in accordance with claim 2 wherein R and $R_1$ are lower alkyl.

4. A compound in accordance with claim 3 wherein $R_2$, $R_3$, $R_4$ and $R_5$ is hydrogen, phenyl or a lower alkyl group.

5. A compound in accordance with claim 4 wherein R and $R_1$ is methyl.

6. A compound in accordance with claim 5 wherein $R_2$, $R_3$, and $R_4$ is hydrogen and $R_5$ is hydrogen or methyl.

7. A compound in accordance with claim 2 wherein R is lower alkyl and $R_1$ is lower hydroxyalkyl.

8. A compound in accordance with claim 7 wherein $R_2$, $R_3$, $R_4$ and $R_5$ is hydrogen, phenyl or a lower alkyl group.

9. A compound in accordance with claim 8 wherein $R_1$ is 2-hydroxypropyl.

10. A compound in accordance with claim 9 wherein R is methyl.

11. A compound in accordance with claim 10 wherein $R_2$, $R_3$ and $R_4$ is hydrogen and $R_5$ is hydrogen or methyl.

* * * * *